US010548996B2

United States Patent
Azab et al.

(10) Patent No.: US 10,548,996 B2
(45) Date of Patent: Feb. 4, 2020

(54) HYDROGELS FOR LOCALIZED RADIOTHERAPY

(71) Applicant: Washington University, St. Louis, MO (US)

(72) Inventors: Abdel Kareem Azab, St. Louis, MO (US); Pilar de la Puente, St. Louis, MO (US); Feda Azab, St. Louis, MO (US)

(73) Assignee: WASHINGTON UNIVERSITY, St. Louis, MO (US)

( * ) Notice: Subject to any disclaimer, the term of this patent is extended or adjusted under 35 U.S.C. 154(b) by 0 days.

(21) Appl. No.: 15/300,158

(22) PCT Filed: Mar. 30, 2015

(86) PCT No.: PCT/US2015/023374
§ 371 (c)(1),
(2) Date: Sep. 28, 2016

(87) PCT Pub. No.: WO2015/149070
PCT Pub. Date: Oct. 1, 2015

(65) Prior Publication Data
US 2017/0209606 A1    Jul. 27, 2017

Related U.S. Application Data

(60) Provisional application No. 61/971,926, filed on Mar. 28, 2014.

(51) Int. Cl.
*A61K 51/00* (2006.01)
*A61M 36/14* (2006.01)
*A61K 51/12* (2006.01)
*A61K 51/06* (2006.01)
*A61K 9/00* (2006.01)

(52) U.S. Cl.
CPC ........ *A61K 51/1244* (2013.01); *A61K 9/0019* (2013.01); *A61K 51/06* (2013.01); *A61K 51/065* (2013.01); *A61K 51/1213* (2013.01)

(58) Field of Classification Search
CPC ............... A61K 51/1244; A61K 51/06; A61K 51/1213; A61K 9/0019; A61K 51/065
USPC ...................................... 424/1.33
See application file for complete search history.

(56) References Cited

U.S. PATENT DOCUMENTS

| 5,163,896 A * | 11/1992 | Suthanthiran ...... A61K 51/1282 600/8 |
| 6,352,682 B2 | 3/2002 | Leavitt et al. |
| 7,413,752 B2 | 8/2008 | Sawhney |
| 2007/0254037 A1* | 11/2007 | Popowski ............ A61K 9/0019 424/490 |
| 2008/0226547 A1* | 9/2008 | Larsen .................. A61K 51/02 424/1.29 |
| 2009/0304587 A1* | 12/2009 | Rubinstein ......... A61K 51/0493 424/1.73 |
| 2011/0104052 A1 | 5/2011 | Barnett et al. |
| 2012/0259153 A1 | 10/2012 | Wang et al. |

FOREIGN PATENT DOCUMENTS

| WO | 2006053836 A1 | 5/2006 |
| WO | 2007052267 A2 | 5/2007 |
| WO | 2015149070 A1 | 10/2015 |

OTHER PUBLICATIONS

Ta et al. J. Control. Rel. 126 (2008) 205-216.*
Azab, A. et al., "Crosslinked chitosan implants as potential degradable devices for brachytherapy: In vitro and in vivo analysis," J. Controlled Release, Apr. 10, 2006, pp. 281-289, vol. 111, No. 3, Elsevier, B.V.
Azab, A. et al., "Prevention of tumor recurrence and distant metastasis formation in a breast cancer mouse model by biodegradable implant of 131I-norcholesterol," J. Controlled Release, 2007, pp. 116-122, vol. 123, Elsevier B.V.
Azab, A. et al., "Biocompatibility evaluation crosslinked chitosan hydrogels after subcutaneous and intraperitoneal implantation in the rat," J. Biomed. Mater. Res., Nov. 2007, pp. 414-422, vol. 83A, No. 2, Wiley Periodicals, Inc.
Bhattarai, N. et al., "Chitosan-based hydrogels for controlled, localized drug delivery," Adv. Drug Deliv. Rev., 2010, pp. 83-99, vol. 62, Elsevier B.V.
International Search Report and Written Opinion dated Jun. 22, 2015 from related International Patent Application No. PCT/US2015/023374; 10 pgs.

* cited by examiner

*Primary Examiner* — Michael G. Hartley
*Assistant Examiner* — Sean R Donohue
(74) *Attorney, Agent, or Firm* — Polsinelli PC

(57) ABSTRACT

Radioactive hydrogels for the delivery of localized radiotherapy, methods of making the radioactive hydrogels, and methods of using the radioactive hydrogels are disclosed. A radioisotope may be conjugated to a high molecular weight molecule, which may be encapsulated in a microparticle, where the microparticle is then dispersed within a hydrogel. The radioactive hydrogel may prevent leakage of the radioisotope to provide radiotherapy to a surgical margin while minimizing damage to surrounding normal tissue.

6 Claims, 9 Drawing Sheets

Iodonation

Encapsulation

Dispersion in hydrogel

HYDROGELS FOR LOCALIZED RADIOTHERAPY

CROSS REFERENCE TO RELATED APPLICATION

This application claims priority of PCT application No. PCT/US2015/023374, filed Mar. 30, 2015, which claims priority to U.S. provisional patent application Ser. No. 61/971,926, entitled "HYDROGELS FOR LOCALIZED RADIOTHERAPY" filed on Mar. 28, 2014, each of which is hereby incorporated by reference in its entirety.

FIELD OF THE INVENTION

The present invention relates to hydrogels for delivery of radioisotopes, in particular, liquid or semi-liquid injectable radioactive hydrogels for the delivery and retention of radioisotopes for cancer radiotherapy.

BACKGROUND

Over the last decades, breast-conserving surgery followed by whole breast irradiation became the standard of care for the treatment of early-stage breast carcinoma. However, the necessity of giving whole breast irradiation for all patients after breast conserving surgery has been questioned, due to serious side effects caused by the external beam radiation. In recent years, many studies compared whole breast irradiation with partial breast irradiation, whether in the form of intraoperative single dose radiation or brachytherapy (the treatment of cancer at a short distance with a radioactive isotope placed on, in, or near the lesions or tumor) applied to the surgical site following surgery. Both methods were found to have the same effectiveness while brachytherapy had less toxic side effects. Conventional brachytherapy for breast conservation requires the insertion of 14 to 20 catheters per procedure and needs complex techniques such as CT guided surgery to place the catheters in the vicinity of the tumor bed. An alternative approach is the MammoSite RTS device, where a single catheter is used to inflate a balloon loaded with the radioisotope in the post lumpectomy cavity immediately or up to 10 weeks post lumpectomy.

Despite clear advantages of brachytherapy over conservative radiotherapy in the treatment of cervical cancer and selected soft tissue sarcomas of the extremities, some major constraints are associated with its implementation in breast cancer and other soft tissue sarcomas. These include the need for general anesthesia or intravenous sedation, complicated placement procedures (especially in the case of interstitial brachytherapy by catheters) and the need for post treatment reexcision for device removal in both methods of catheters and MammoSite, and/or to treat infections associated with the device. Therefore, an alternative mode of local radiotherapy is warranted.

Similarly, cancers of the brain and the central nervous system affect approximately 135,000 people in the USA who are living with a diagnosis of a malignant brain tumor. The current standard of care includes maximal safe surgical resection, followed by a combination of radiation and chemotherapy; resulting in median survival of 14.6 months and the percentage of patients alive at 2 years is approximately 26%.

Due to the short mean survival, frequent recurrences, and poor prognosis associated with the tumors, new therapeutic strategies were investigated consecutively including local drug delivery approaches. Interstitial radiotherapy (brachytherapy) has been suggested using $^{125}$I and $^{192}$Ir temporary and permanent implants. Interstitial high-dose-rate therapy needed complicated implantation techniques such as CT-guided surgery, and was frequently associated with relatively high toxicity. Interstitial low-dose-rate therapy, temporary implants are preferred as permanent implants bear an increased risk of prolonged edema. Brachytherapy with temporary implants may lead to prolonged survival in patients with recurrent glioma, but it is associated with morbidity and relatively high costs. It is associated with fewer side effects compared to high-dose-rate approaches, although randomized approaches are lacking. A third approach is the GliaSite, a technological alternative to seed-implantation, in which radiation is applied via a surgically inserted balloon catheter which is filled with a liquid $^{125}$I containing solution to deliver a high-dose-rate therapy. This device is showing promising results in the recurrent disease setting; however, this approach has some shortcomings in terms of uncertainties of dose distribution, side effects and the invasiveness in a highly palliative treatment setting.

Despite the clear advantage of the brachytherapy with solid hydrogel implants, previous solid implants did not fill the surgical cavity which raised questions about the homogeneity of the radiation in the surgical margins. Another limitation of the solid hydrogels was the leakage of the radioactivity to adjacent normal tissues which was observed in the first week after implantation. Therefore, an efficient way to prevent leakage of radioactivity from the implant during the treatment is warranted. Due to the short mean survival, frequent recurrences, and poor prognosis, particularly with breast cancer and glioma, new therapeutic strategies are warranted.

SUMMARY

One aspect of the present invention encompasses a radioactive hydrogel including at least one radioisotope, at least one high molecular weight molecule conjugated to the radioisotope, at least one microparticle encapsulating the radioisotope conjugated to the at least one high molecular weight molecule, and an injectable hydrogel. The at least one microparticle is disbursed within the injectable hydrogel, and the at least one radioisotope is retained within the injectable hydrogel to deliver localized radiotherapy within a surgical cavity. The radioactive hydrogel may further include a small molecule distributed within the injectable hydrogel, the small molecule selected from the group consisting of a chemotherapeutic, a radiosensitizer, and combinations thereof. The at least one radioisotope may be selected from $^{131}$I, $^{124}$I, $^{126}$I, and $^{103}$Pd. The at least one high molecular weight molecule may be selected from polytyrosine, serum albumin, and polymers with chelating residues. The at least one microparticle may be selected from alginate, poly-acrylate, poly-metacrylate, poly-carbophil, Carbopol, poly-styrene, and poly-sulfonate. The injectable hydrogel may include chitosan. The surgical cavity may be a rescission site of a soft tissue sarcoma. The soft tissue sarcoma may be selected from the group consisting of glioma and breast cancer.

Another aspect of the present invention encompasses a method of making radioactive hydrogels including conjugating at least one radioisotope to at least one high molecular weight molecule, encapsulating the at least one radioisotope conjugated to the at least one high molecular weight molecule in at least one microparticle, and disbursing the at least one microparticle within an injectable hydrogel. The at least one radioisotope may be retained within the injectable hydrogel to deliver localized radiotherapy to a surgical cavity. The at least one radioisotope may be selected from $^{131}$I, $^{124}$I, $^{126}$I, and $^{103}$Pd. The at least one high molecular weight molecule may be selected from poly-tyrosine, serum albumin, and polymers with chelating residues. The at least one microparticle may be selected from alginate, poly-acrylate, poly-metacrylate, poly-carbophil, Carbopol, poly-styrene, and poly-sulfonate. The injectable hydrogel may include chitosan. The surgical cavity may be a rescission site of a soft tissue sarcoma. The soft tissue sarcoma may be selected from the group consisting of glioma and breast cancer.

Another aspect of the present invention encompasses a method of delivering radiotherapy including resecting a soft tissue sarcoma to create a surgical cavity and injecting a radioactive hydrogel into the surgical cavity. The radioactive hydrogel may include at least one radioisotope, at least one high molecular weight molecule conjugated to the radioisotope, at least one microparticle encapsulating the at least one radioisotope conjugated to the at least one high molecular weight molecule, and an injectable hydrogel. The at least one microparticle may be disbursed within the injectable hydrogel, and the at least one radioisotope may be retained within the injectable hydrogel to deliver localized radiotherapy to a region of interest. Furthermore, the radioactive hydrogel may biodegrade over time and may not be removed from the surgical cavity. The at least one radioisotope may be selected from $^{131}$I, $^{124}$I, $^{126}$I, and $^{103}$Pd. The at least one high molecular weight molecule may be selected from poly-tyrosine, serum albumin, and polymers with chelating residues. The at least one microparticle may be selected from alginate, poly-acrylate, poly-metacrylate, poly-carbophil, Carbopol, poly-styrene, and poly-sulfonate. The injectable hydrogel may include chitosan.

BRIEF DESCRIPTION OF THE DRAWINGS

The following figures illustrate various aspects of the disclosure.

Corresponding reference characters and labels indicate corresponding elements among the views of the drawings. The headings used in the figures should not be interpreted to limit the scope of the claims.

DETAILED DESCRIPTION

Provided herein are radioactive hydrogels for the delivery of localized radiotherapy, methods of making the radioactive hydrogels, and methods of using the radioactive hydrogels. In an aspect, a radioisotope may be conjugated to a high molecular weight molecule, which may be encapsulated in a microparticle. The microparticle may be then dispersed within an injectable hydrogel to form the radioactive hydrogel. The radioactive hydrogel may prevent leakage of the radioisotope and provide radiotherapy to a surgical margin while minimizing damage to surrounding normal tissue.

The radioactive hydrogel may be an alternative to external-beam radiation and current brachytherapy devices in localized (non-metastatic) tumors. The radioactive hydrogel may be an adjuvant therapy after surgery. In an aspect, the radioactive hydrogel is injectable and reserves the need for surgical implantation. In another aspect, the radioactive hydrogel irradiates the surgical margin of the surgical cavity continuously and eliminates the need for repeated visits to receive radiotherapy by external beam radiation or by brachytherapy. The radioactive hydrogel may allow more efficient treatment by introducing the radioactive dose to the direct vicinity of the surgical margin of the surgical cavity, while preventing or reducing damage to adjacent normal tissues. In an aspect, the radioactive hydrogel is biodegradable and prevents the need for surgical removal of a device and reduces the possibility of contamination compared to temporary brachytherapy devices such as catheters and balloons. The radioactive hydrogel may also promote wound healing after the radioisotope has decayed. The production of the radioactive hydrogel may be cheaper compared to the expensive machinery needed for external beam radiation and brachytherapy. In addition, highly trained professionals may not be needed for the application of the radioactive hydrogels.

Figure 1A:
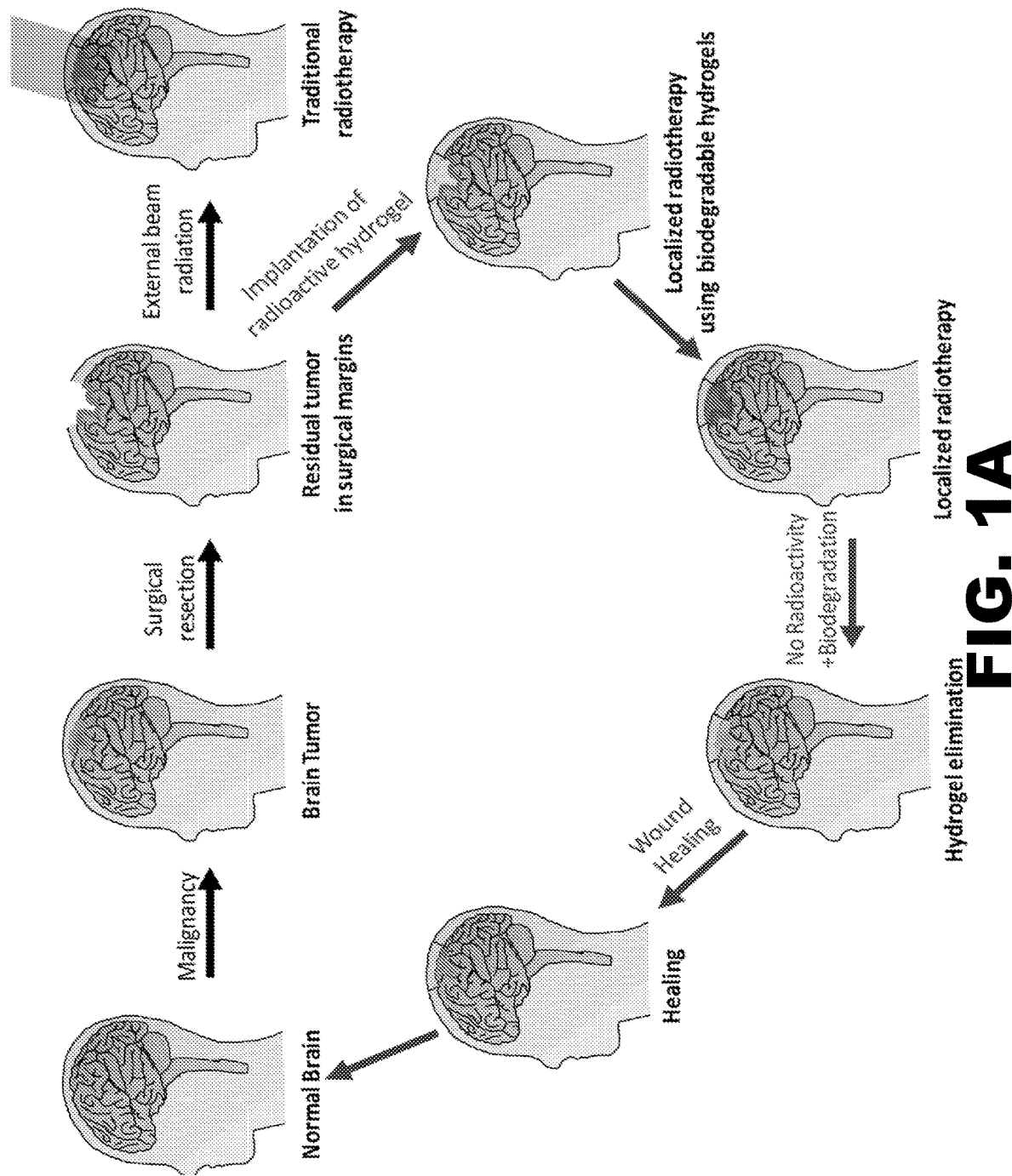
FIGS. 1A-1B are illustrations of a method of localized radiotherapy using biodegradable hydrogels in the brain (FIG. 1A) and breast (FIG. 1B).
Figure 1B:
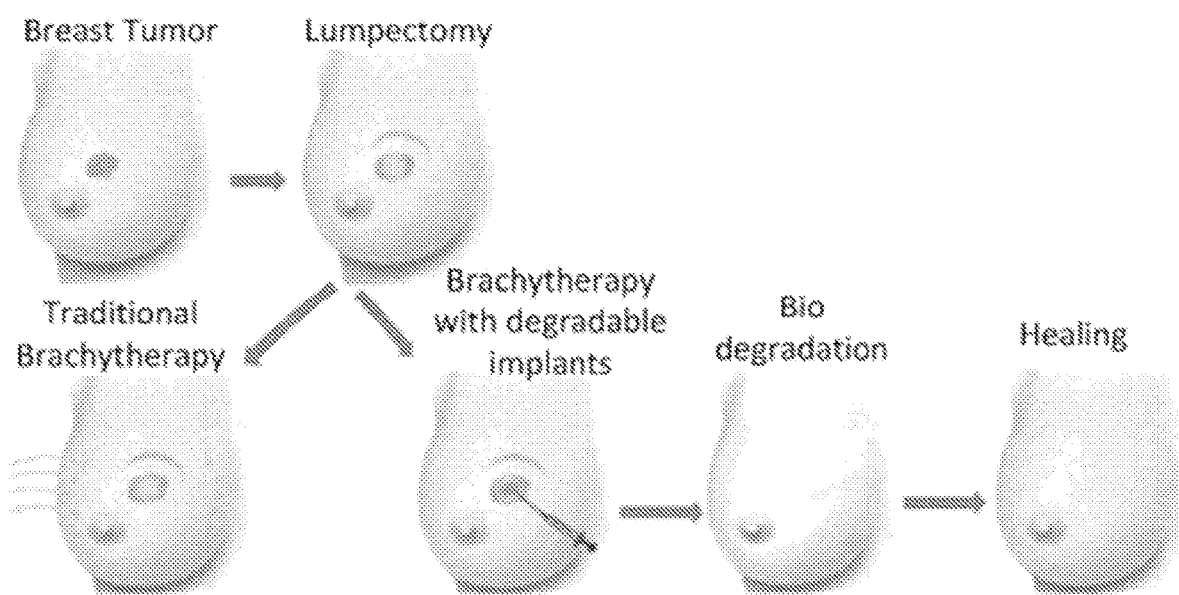

The radioactive hydrogels may be liquid or semi-solid which can be injected to fill a surgical cavity and produce more homogeneous radiation. In particular, the radioactive hydrogel is an injectable and biodegradable hydrogel made from cross-linked poly-saccharides, which may be loaded with radioisotope to be implanted in the surgical cavity left after tumor resection. The radioactive hydrogel may facilitate localized radiotherapy in the surgical margin of the surgical cavity. In an aspect, the hydrogel will keep the radioisotope unreleased during the treatment, but after the decay of the radioisotope, the hydrogel will biodegrade and facilitate wound healing, as illustrated in FIGS. 1A-1B.

I. Radioactive Hydrogel

A radioisotope may be conjugated to a high molecular weight (MW) molecule, which may be encapsulated in a microparticle. The microparticle may then be dispersed within an injectable hydrogel to form the radioactive hydrogel.

The radioactive hydrogel includes a radioisotope. In an aspect, a short half-life radioisotope may be used as the radioisotope since this will allow the decay of the radioactivity before the start of the biodegradation of the hydrogel. Moreover, the radioisotope may have a beta-decay which is characterized by limited tissue penetration providing localized effect to the surgical margin of the surgical cavity and reducing damage in normal tissue. Non-limiting examples of the radioisotope include $^{131}$I, $^{124}$I, $^{126}$I, $^{103}$Pd, halogen radioisotopes, and metal radioisotopes. The halogen radioisotopes, and metal radioisotopes. The radioisotope may be $^{131}$I, which has a half-life of 8 days, in one aspect. The type and dosage of the radioisotope selected for use may depend on the cancer type and tumor size being treated.

The radioisotope may be conjugated to a high molecular weight molecule, as conjugation to a large molecule may decrease the diffusion of the radioisotope through the hydrogel and decrease the leakage. In an aspect, the high molecular weight molecule may have a molecular weight greater than about 4 kD. The high molecular weight molecule may be selected to be able to chemically bind the radioisotope and to be biocompatible.

Non-limiting examples of high molecular weight molecules include proteins and polymers, such as poly-tyrosine, human serum albumin, and polymers with chelating residues. In an aspect, the high molecular weight molecule may be poly-tyrosine for conjugation to halogen radioisotopes. This conjugation may increase the efficiency of iodination (using $Na^{131}I$ and chloramines-T), where $^{131}I$ may be conjugated to poly-tyrosine. In other aspects, human serum albumin may be used for conjugation to halogen radioisotopes and polymers with chelating residues may be used for conjugation to metal radioisotopes. The type of high molecular weight molecule used for conjugation may depend on the radioisotope selected for the particular treatment.

In another aspect, the radiolabeled high MW molecule may be encapsulated in highly cross-linked microparticles before dispersion in the hydrogel. Diffusion of the radiolabeled high MW molecule in the highly-cross-linked microparticle may be negligible, and the release of entire microparticles from the hydrogel may be negligible as well, due to the relatively large size of the microparticle. Any microparticle which may be crosslinked and may promote a chemical interaction with the hydrogel may be used. In one aspect, the microparticles may be about 0.1 µm to about 10 µm in size. In various other aspects, the microparticles may range in size from about 0.1 µm to about 1 µm, from about 0.5 µm to about 5 µm, about 1 µm to about 8 µm, and about 5 µm to about 10 µm.

The microparticles may be negatively charged polymers that may be crosslinked by positively charged ions. The microparticles may also interact chemically with the hydrogel. Non-limiting examples of polymers that may be used for the microparticles include poly-acrylates, poly-metacrylates, poly-carbophil, Carbopol, poly-styrene, poly-sulfonate, derivatives thereof, and any other negatively charged biocompatible polymer that may interact with the hydrogel. In an aspect, the highly cross-linked microparticle may include calcium and alginate. The chemical interaction between the microparticles and a hydrogel may limit the diffusion of the microparticles and their content from the radioactive hydrogel. In an aspect, the chemical interaction between alginate microparticles and a chitosan hydrogel may limit the diffusion of the microparticles and their content from the radioactive hydrogel. All together, these strategies may ensure the prevention of release of the radioisotope from the hydrogel.

The injectable hydrogel of the radioactive hydrogel may include cross-linked polysaccharides. Chitosan, a natural polysaccharide, has been used in a variety of medical uses such as orthopedics, tissue engineering, and wound healing. In one aspect, chitosan may be used as the base of a radioactive hydrogel drug delivery system due to its biocompatibility and biodegradability. In another aspect, the chitosan hydrogel may begin degrading around about 2 months after implantation. The timing of this degradation would allow for the radiation of the radioisotope to deplete before being released from the hydrogel due to degradation. In one aspect, chitosan radioactive hydrogels may be loaded with $Na^{131}I$, $^{131}I$-poly-tyrosine and/or $^{131}I$-poly-tyrosine encapsulated in calcium-alginate microparticles.

Figure 3:
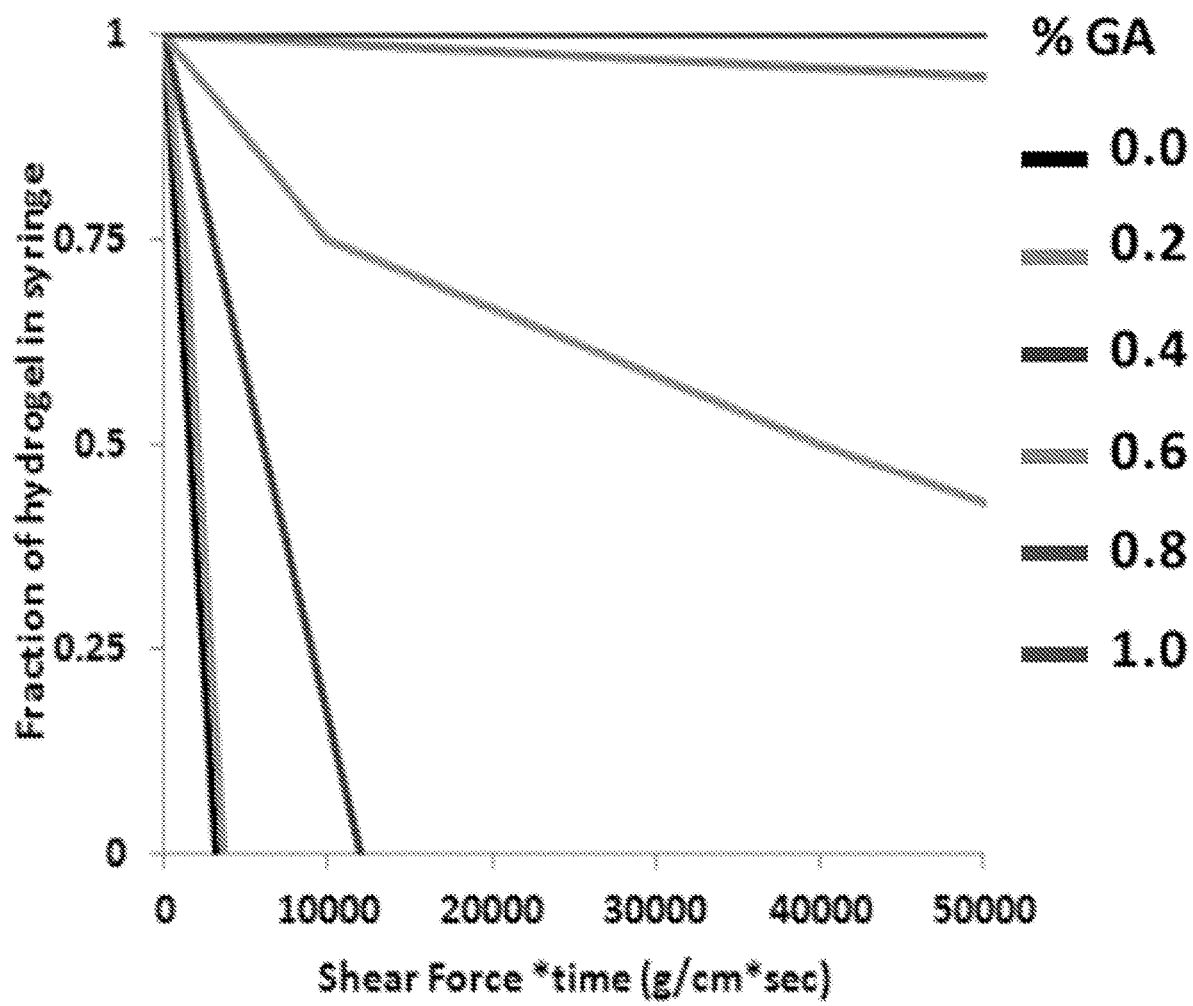
FIG. 3 is a graph of the injectability of the hydrogels, measured by the time needed for emptying the syringe.

The radioactive hydrogels may be cross-linked polysaccharide hydrogels cross-linked using different concentrations of a cross-linker. Non-limiting examples of cross-linkers includes glutaraldehyde, sodium triphosphate, sodium oxalate, or any other compound suitable to cross-link chitosan. In various aspects, the concentration of the cross-linker may ranges from about 0% to about 1%. In one aspect, the concentration of the cross-linker may be about 0.4% glutaraldehyde. The concentration of the cross-linker may influence the viscosity, and by extension the injectability, of the hydrogel as illustrated in FIG. 3. The radioactive hydrogel may be provided in a liquid or semi-solid form to be injected into a surgical cavity.

The radioactive hydrogel may further include a small molecule to be released from the radioactive hydrogel. The small molecule may not be retained in the radioactive hydrogel for an extended period of time. In an aspect, the small molecule may diffuse from the radioactive hydrogel into the surgical cavity and the surrounding tissue.

The type of small molecule incorporated into the radioactive hydrogel may depend on the type of cancer to be treated. By way of non-limiting example, the small molecule may be a chemotherapeutic compound used in the treatment for a specific cancer. In various aspects, the small molecule may be a chemotherapeutic, a radiosensitizer, or any other therapeutic compound that may work in combination with radiotherapy. In one aspect, the chemotherapeutic may be temozolomide (TMZ). Non-limiting examples of the small molecule that may be used in glioma include temozolomide, procarbazine, carmustine, vincristine, and lomustin. Non-limiting examples of the small molecule that may be used in breast cancer include doxorobicin, paclitaxel, cyclophosphamide, methotrexate, flurouracil, and others. The small molecule may be released from the radioactive hydrogel in conjunction with the radiation emitted by the radioisotope within the radioactive hydrogel. In an aspect, the small molecule may provide synergistic therapy in combination with the radiotherapy.

II. Method of Producing Radioactive Hydrogel

The method of producing a radioactive hydrogel may include, but is not limited to, conjugating a radioisotope to a high molecular weight molecule, encapsulating the radioactive high molecular weight molecule in a microparticle, and incorporating the microparticle in a hydrogel.

The microparticles may be formed by crosslinking a microparticle base with a crosslinking agent. In one aspect, alginate microparticles may be prepared by inducing the cross-linking of an alginate solution with calcium chloride. When sodium alginate solution is added into a solution containing calcium ions, the calcium ions replace the sodium ions in the alginate polymer, resulting in cross-linking of the alginate. Alginic acid sodium salt obtained from brown algae, sodium bicarbonate, and calcium chloride may be used to form alginate (Alg) microparticles in an aspect. EDTA may be used to dissolve alginate microparticles. In another aspect, various alginate concentrations (about 10-100 mg/ml) may be dissolved in about 0.1M sodium bicarbonate in two steps: 1) grinding the alginate using any known device including, but not limited to, a mortar; and 2) mixing the ground alginate with the about 0.1M sodium bicarbonate using any known stirring device including, but not limited to, a magnetic stirrer. Finally, the resulting sodium alginate solution may be added drop wise into an about 0.1 M calcium solution using any known device including, but not limited to, a 30G needle. The resulting alginate microparticles may then be washed about three times with a rinsing solution including, but not limited to, DDW. Radioactive high MW molecules may be loaded into the sodium alginate solution and subsequently dropped into the calcium chloride solution to form microparticles encapsulating the radioactive high MW molecules in an aspect. The resulting microparticles encapsulating the radioactive high MW molecules may be dispersed into the chitosan hydrogels in an aspect.

The hydrogel may be formed by crosslinking polysaccharides with a crosslinking agent. Low molecular weight chitosan (Ct), about 99.7% acetic acid, and about 25% glutaradehyde solution (GA) may be used for preparation of the chitosan hydrogels, in one aspect.

In one aspect, injectable radioactive hydrogels may be produced by dissolving about 1 g of chitosan in about 100 ml of about 0.1 M acetic acid. First, the chitosan solution may be heated to about 100° C. and then, while the solution is being stirred, different glutaraldehyde solution concentrations (about 0.1-5% w/v in water) may be added. The microparticles encapsulating the radioactive high MW molecules may be dispersed within the chitosan solution during this time. A hydrogel may be immediately formed, and stirring may then be stopped thereafter. The chitosan hydrogels may be allowed to stabilize for about 4 hours.

III. Method of Delivering Radiotherapy

The cross-linked hydrogel may form a radioactive hydrogel which may be suitable for injection to fill the surgical cavity, and may additionally be biodegradable in vivo upon completion of the radiotherapy. The radioactive hydrogel may inhibit leakage of the radioisotope to normal tissues during the treatment. In an aspect, conjugation of the $^{131}$I to poly-tyrosine, and its encapsulation into calcium-alginate micro-particles before introducing it to the chitosan hydrogel may prevent the leakage of radioisotope.

The radioactive hydrogel may be used after the rescission of a non-metastatic tumor or any other tumor that can be removed by surgery and leaves a defined surgical cavity after surgery. These tumors may include, but are not limited to breast tumors, brain tumors, and any other soft tissue sarcoma. Once a tumor is removed, the radioactive hydrogel may be injected into the surgical cavity and may contact the surgical margin of the surgical cavity. The radioactive hydrogel may keep the radioactivity localized to the site of the surgical cavity and the surgical margin during treatment, and may facilitate localized radiotherapy at the surgical margins. FIG. 1A illustrates the replacement of external beam radiation with radioactive hydrogels in the treatment of brain tumors. FIG. 1B illustrates the replacement of external beam radiation with radioactive hydrogels in the treatment of breast cancer.

The radioisotope may be retained within the radioactive hydrogel until the radiation decays. The radioactive hydrogel may release radiation for a period of about 5 days to about 20 days after injection. In an aspect, the radioactive hydrogel may release radiation over a period of about 8 days. The rate of decay will be dependent on the half-life of the radioisotope within the radioactive hydrogel. The hydrogel may begin to biodegrade after the radioisotope has decayed. In an aspect, the hydrogel may decay between about 20 days and about 6 months after injection. The hydrogel may also help with wound healing during degradation of the hydrogel.

The radioactive hydrogels may inhibit tumor growth and prevent tumor recurrence more effectively compared to conventional radiotherapy. In an aspect, the radioactive hydrogels may prevent the recurrence of glioma. The radioactive hydrogels may be more efficacious in inhibiting tumor cell growth, prevent tumor recurrence, and induce fewer side effects compared to conventional radiotherapy. In an aspect, the dose of $^{131}$I loaded into the radioactive hydrogels may be adjusted and the radioactive dose at different distances from the radioactive source may be calculated.

The radioactive hydrogels may reduce or prevent glioma, breast cancer, or other soft tissue sarcoma progression and recurrence. In an aspect, potential side effects of the radioactive hydrogels in adjacent normal tissues and distant organs may be reduced compared to traditional radiotherapy.

In an aspect, small molecules such as chemotherapeutics and radiosensitizers may be released from the radioactive hydrogel to surrounding tissues in conjunction with the radiotherapy delivered from the radioactive hydrogels. This release may provide a synergistic effect in the surgical cavity between the small molecule and the radioisotope.

EXAMPLES

Example 1

Preparation of the Chitosan Hydrogels

The following materials were used to prepare the hydrogels. Unless stated otherwise, all materials were purchased from Sigma (St. Louis, Mo., USA). Chitosan (Ct) low molecular weight, acetic acid 99.7%, and glutaradehyde solution 25% (GA) were used for preparation of the chitosan hydrogels. Alginic acid sodium salt from brown algae, sodium bicarbonate, and calcium chloride were used for elaboration of alginate (Alg) microparticles. EDTA was used to dissolve the alginate microparticles. Albumin-fluorescein isothiocyanate conjugate (Alb-FITC), fluorescein isothiocyanate (FITC) and cresyl violet acetate (CV) from MP Biomedicals (Solon, Ohio, USA) were used for evaluation of in vitro release.

This example provides for the preparation of chitosan hydrogels used to contain microparticles with radioactive high MW molecules. To form the injectable hydrogels, chitosan (1 g) was dissolved in 100 ml of 0.1M acetic acid. First, the chitosan solution was heated to 100° C. and then, while the solution was being stirred, different glutaraldehyde solution concentrations (0.1-5% w/v in water) were added. A hydrogel was immediately formed, and stirring was stopped thereafter. The chitosan hydrogels were allowed to stabilize for 4 hours before characterization.

Example 2

Crosslinking and Shear-stress Characterization of Chitosan Hydrogels

To evaluate the crosslinking and shear-stress of the chitosan hydrogels, the following experiment was conducted. Crosslinking characterization was developed by evaluating the viscosity of the chitosan hydrogels. Chitosan hydrogels of each group were characterized by three viscosity levels in liquid, semi-solid or solid. The injectability of the chitosan hydrogels was analyzed by using a shear-stress characterization. The shear-stress technique consisted on the introduction of 4 ml chitosan hydrogel in a 5 ml syringe. A constant force (200 g or 500 g) was applied on top of the syringe and the time needed for dispersing various amounts of hydrogel (¼, ²⁄₄, ¾, and full volume of syringe contents) were measured. The results (amount of hydrogel vs time*force) showed the shear-stress properties of the chitosan hydrogels. Measurements were made in triplicate for each group.

Example 3

Preparation of the Alginate Microparticles

This example provides for the preparation of alginate microparticles. The alginate microparticles were produced by inducing the cross-linking of an alginate solution with calcium chloride. When sodium alginate solution was added into a solution of calcium ions, the calcium ions replaced the sodium ions in the alginate polymer. Various alginate concentrations (10-100 mg/ml) were dissolved in 0.1M sodium bicarbonate in two steps. First, by being grinded in a mortar and then, by being mixed with a magnetic stirrer. Finally, alginate solution was added drop wise with a 30G needle in a 0.1M calcium solution. The alginate microparticles were washed three times with DDW.

Example 4

Alginate Microparticles Characterization: Size and Encapsulation Efficiency

The following experiments were performed to determine the size and encapsulation efficiency of the alginate microparticles. The morphological examination of the microparticles was performed by optical microscope (Olympus ix70 inverted microscope). The size of alginate microparticles was measured from microscopic images (QI-CAM Fast 1394 Digital Camera) by using image analysis software (Image J).

Encapsulation efficiency was measured by dissolving the microparticles in 0.1M EDTA. 5% CV was dissolved in the alginate solution before dropping the alginate solution into the calcium chloride solution. CV encapsulation was measured by spectrophotometer reader at 595 nm. Cresyl violet-alginate solutions were used as controls for each group of study. Measurements were made in triplicate for each group.

Example 5

In Vitro Release Studies of Chitosan Hydrogels Loaded with Alginate Microparticles To determine the release of large molecules from the hydrogels, the following experiment was conducted. The chitosan hydrogels with the best injectability properties were analyzed naïve or loaded with the alginate microparticles with the best encapsulation efficiency. The in vitro release studies were developed by using a large-size molecule such as albumin and a small-size molecule as cresyl violet to detect the efficacy in both encapsulation settings. Albumin is not detectable by fluorescence reader or spectrophotometer, thus FITC was labeled to albumin. Alb-FITC, FITC, and CV were loaded in alginate solution either by being dropped into calcium chloride to make microparticles or by being included directly into the chitosan hydrogel. When Alb-FITC, FITC and CV alginate microparticles were made, they were dispersed into the chitosan hydrogels. Finally, the hydrogels were included in PBS (pH 7.4) at 4° C. and were kept shaking at dark for 42 days. Alb-FITC, FITC and CV were added to the PBS solution that contains chitosan naïve hydrogels as control, and also chitosan naïve hydrogels were included in PBS as blank. Measurements were made in triplicate for each group, which are defined in Table 1. Different time points were measured to analyze short and long-term release. At 0, 1, 2, 4, 8, and 24 h, for short-term release, and 0, 0.33, 1, 2, 3, 7, 14, 21, 28, 42 days for long-term release, samples from the PBS solution that surrounded the chitosan hydrogels were analyzed by fluorescence reader (Alb-FITC and FITC) at 485/516 nm or spectrophotometer (CV) at 595 nm. The % release was calculated as follows: % Release=(Chitosan hydrogel−Blank)/(Control−Blank)*100

TABLE 1

In vitro release studies

| Dye | Ct hydrogel | Control | Blank |
|---|---|---|---|
| FITC | FITC-Ct hydrogels<br>Ct hydrogels FITC-alg microparticles | PBS-FITC | PBS |
| Alb-FITC | Alb-FITC-Ct hydrogels<br>Ct hydrogels Alb-FITC-alg microparticles | PBS-Alb-FITC | PBS |
| CV | CV-Ct hydrogels<br>Ct hydrogels CV-alg microparticles | PBS-CV | PBS |

Example 6

Statistical Analysis

Data was expressed as means±standard deviation. The SPSS Statistics 17.0 program was used to determine statistical significance between groups; $p<0.05$ was considered significant. The Kolmogorov-Smirnov and Levene tests were used in the parametric normality and homoscedasticity assumptions respectively, after checking the criteria for parametric analysis, which was performed using Student's t-test for independent samples.

Example 7

Cross-linking of Hydrogel

Figure 2:
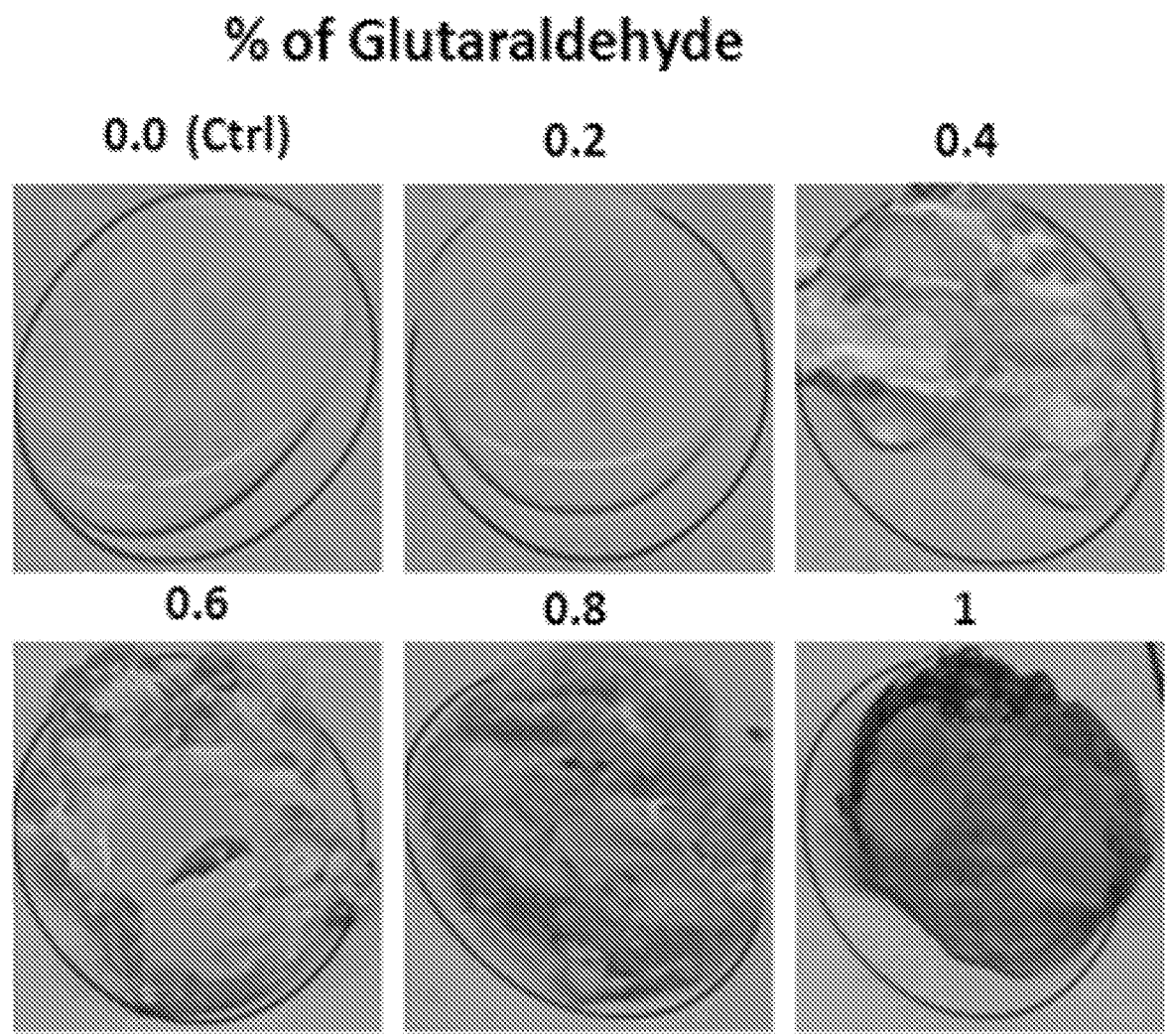
FIG. 2 are photographic images showing the physical appearance of chitosan solution cross-linked with glutaraldehyde at 0.0, 0.2, 0.4, 0.6, 0.8, and 1.0%.

To determine the amount of glutaraldehyde for cross-linking to achieve the desired hydrogel properties, the following experiment was performed. Solid hydrogel implants were previously prepared using cross-linking with high concentration of glutaraldehyde, and the new injectable radioactive hydrogels were prepared using lower concentrations of the cross-linker glutaraldehyde. FIG. 2 shows that the physical appearance of non-cross-linked chitosan was a viscose liquid, and that cross-linking of chitosan increased the viscosity and forming hydrogels up to a formation of solid hydrogels at 1%.

In addition, the injectability of the different hydrogels produced by cross-linking with glutaraldehyde was tested by loading the different hydrogels into syringes and applying constant force on the syringe. The time needed for the dispensing of the hydrogel from the syringe was recorded. FIG. 3 shows that the non-cross-linked solution was dispensed rapidly out, while increased concentrations of glutaraldehyde increased the time needed for the injection. At concentrations of 0.8% and 1% the hydrogels were more solid and did not go through the syringe. The optimal gel for injection and filling of the surgical cavity may be the one cross-linked with 0.4% glutaraldehyde.

Example 8

Radioisotope Release

Figure 4:
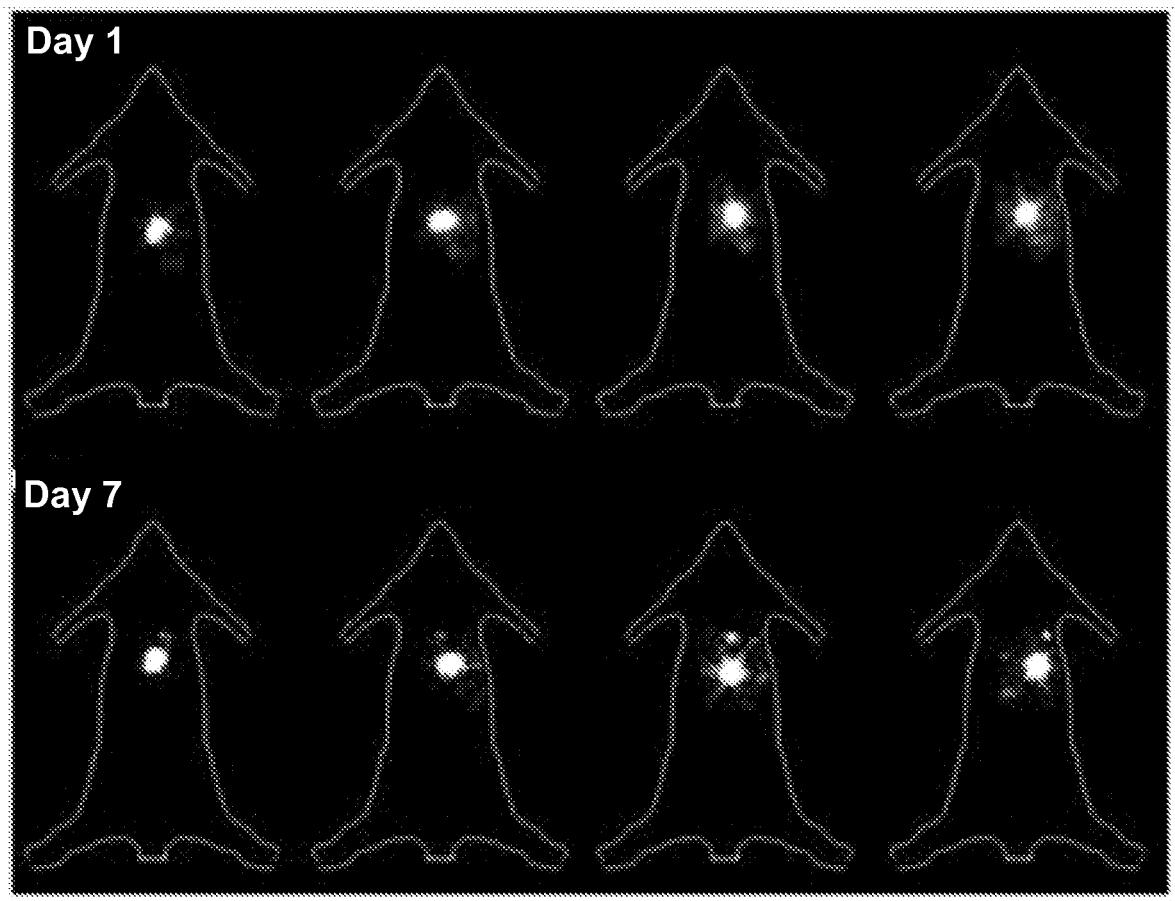
FIG. 4 shows radiographic imaging of rats implanted with solid hydrogels loaded with $^{131}$I-nor-cholesterol (small molecule).

The release of non-encapsulated $^{131}$I-nor-cholesterol (a small molecule) from the solid chitosan hydrogels to adjacent normal tissues in rats was assessed in the following experiment. FIG. 4 shows that there was a radioactive leakage from the implant starting at Day-1 that becomes more evident at Day-7. Previous studies showed that the degradation of the hydrogel at that point is minimal; however, a leakage of radioactivity is still observed. Therefore, a development of a vehicle which will eliminate the leakage of radioactivity was warranted. To overcome this limitation two strategies were proposed: the first was to conjugate the $^{131}$Iodine to poly-tyrosine, as conjugation to a large molecule will decrease the diffusion of the radioisotope through the hydrogel and decrease the leakage. The second strategy was to encapsulate the labeled protein in highly cross-linked calcium-alginate microparticles before dispersion in the hydrogel. It was hypothesized that the diffusion of the labeled peptide in the highly-cross-linked microparticle would be negligible, and the release of entire microparticles from the hydrogel would be negligible as well, due to the relatively large size of the microparticle and the chemical interaction between the alginate and the chitosan which will limit the diffusion of the microparticles and their content. All together, these two strategies may ensure the prevention of release of the radioactive Iodine from the hydrogel.

Figure 5:
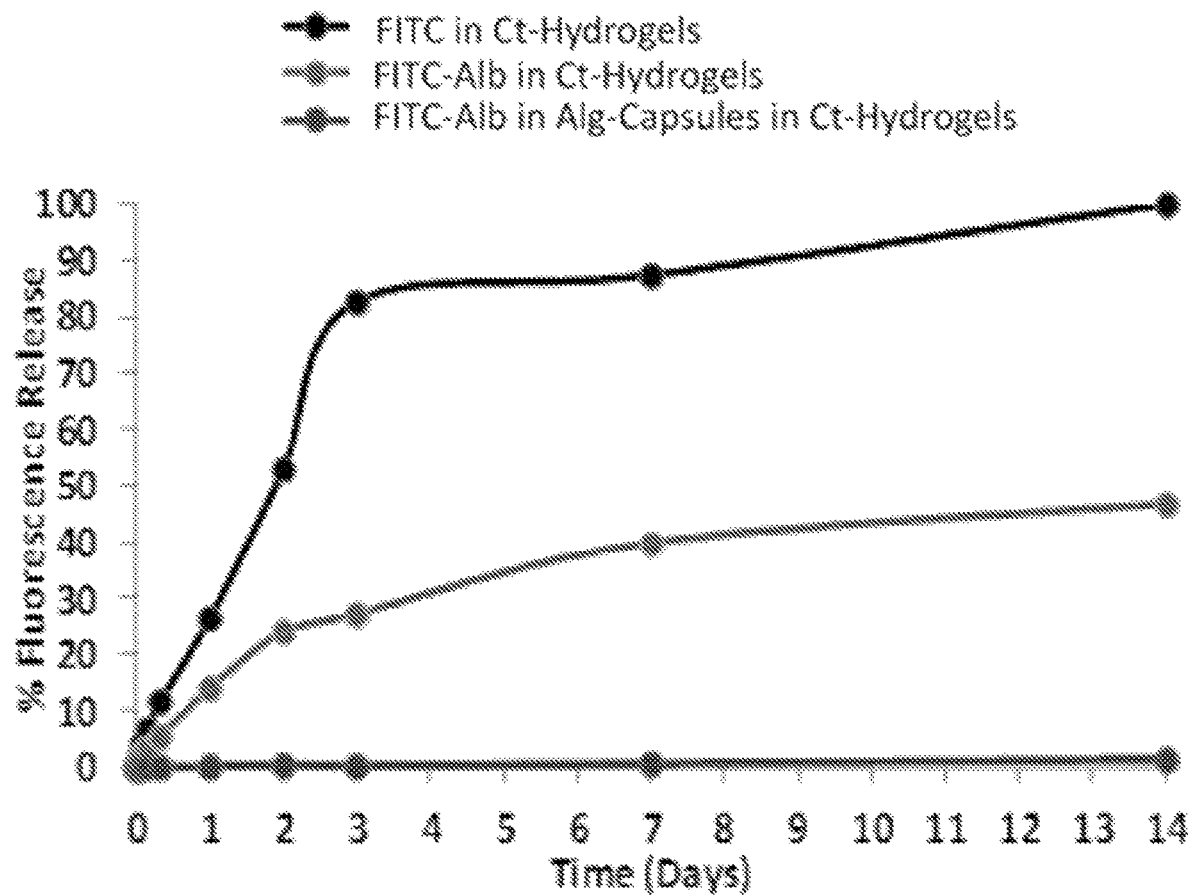
FIG. 5 is a graph of the release of fluorescence from chitosan hydrogels loaded with free fluorescein, FITC-BSA, and FITC-BSA encapsulated.

To assess these concepts, the release of fluorescence to the surrounding media was tested from chitosan hydrogels containing free-fluorescein, fluorescien-conjugated to bovine serum albumin (FITC-Alb), and FITC-Alb encapsulated in calcium-alginate microparticles. FIG. 5 shows that the relative release of FITC-Alb was less than half of the relative release of fluorescein at all the time points tested; while the encapsulation of FITC-Alb in calcium-alginate micro-capsules completely prevented the release of fluorescence to the media for two weeks.

Hydrogels were produced by cross-linking chitosan with increasing concentrations of glutaraldehyde, sodium triphosphate, and sodium oxalate; calcium-alginate microcapsules were produced; and the physicochemical properties of the hydrogels and the microparticles were optimized.

Example 9

Chemotherapeutic Release

Figure 7A:
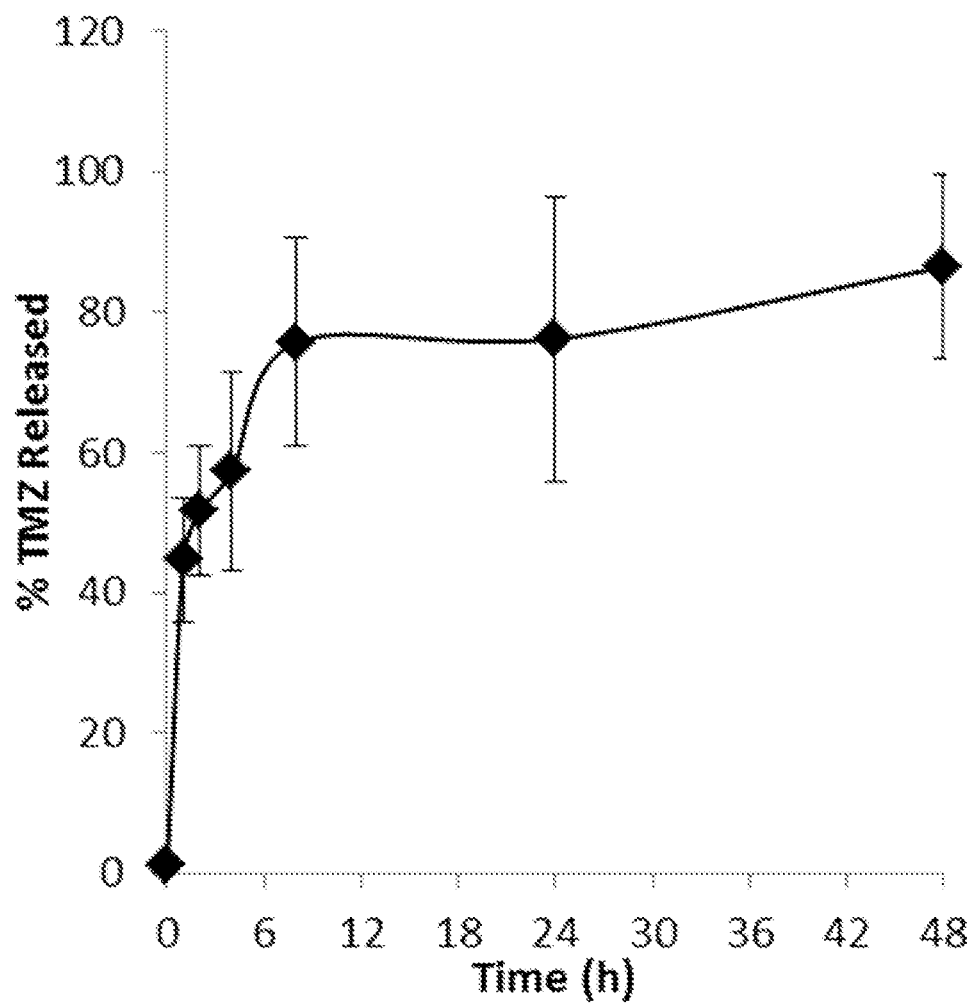
FIGS. 7A-7B are graphs showing the release profile of TMZ from the hydrogel (FIG. 7A) and the effect of TMZ on glioma cells in vitro (FIG. 7B).
Figure 7B:
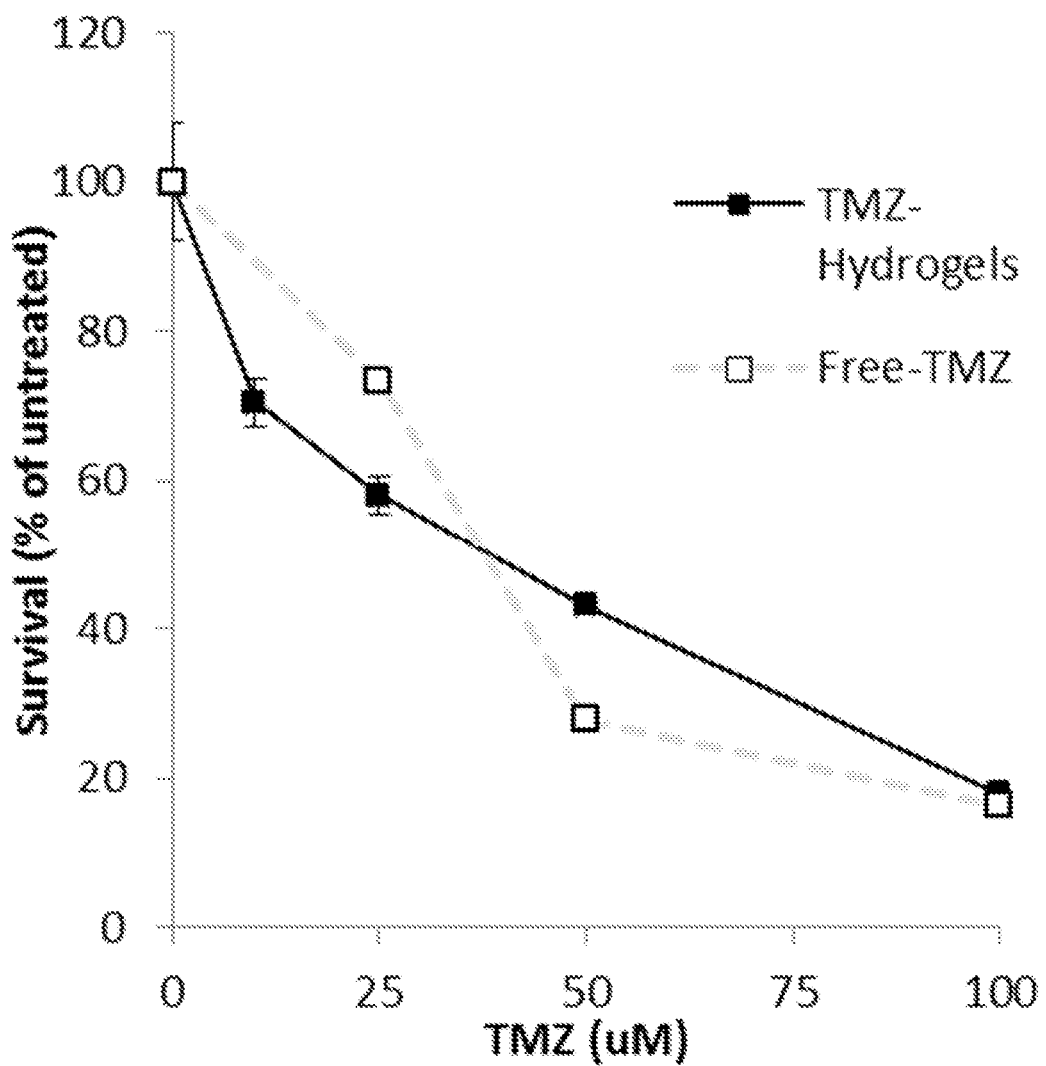

To assess the release and effectiveness of a chemotherapeutic from the hydrogels, the following experiments were conducted. The percent release of temozolomide (TMZ) from a hydrogel was measured over 48 hours (FIG. 7A). FIG. 7A illustrates that while radioactivity is maintained in the hydrogel for weeks, chemotherapy like TMZ can be released within 24 from the hydrogel to promote localized high level of chemotherapy in the tumor region. FIG. 7B shows the effect of TMZ on the 24-hours survival of glioma cells in vitro, when applied as a free drug into the solution or when released from the hydrogel. The effect of TMZ on glioma cells was similar when delivered as a free drug or when released from the hydrogel. These results demonstrate that the hydrogel can promote localized treatment with chemotherapy, in addition to its radio-therapeutic properties.

Prophetic Example 1

The physicochemical and biological properties of the injectable, biodegradable hydrogel may be optimized. The hydrogel may be cross-linked using other cross-linkers such as sodium oxalate and sodium triphosphate. Increased concentrations of each cross-linker may be used for cross-linking of chitosan and their injectability properties may be characterized. This is due to the known high toxicity of glutaraldehyde, and that residual traces of free glutaraldehyde might induce local tissue response in vivo, while both oxalate and triphosphote are considered safe cross-linkers.

The release profiles of radioactivity from chitosan hydrogels loaded with Na$^{131}$I, $^{131}$I-poly-tyrosine, and $^{131}$I-poly-tyrosine encapsulated in calcium-alginate micro-particles may be studied in vitro.

Figure 6:
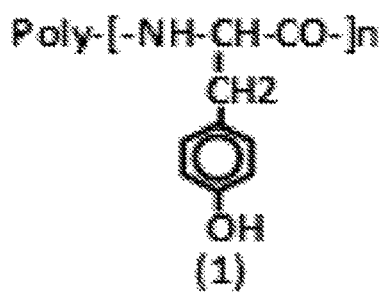
FIG. 6 is a schematic illustration of the production of a radioactive hydrogel implant for localized radiotherapy.
Figure 6:
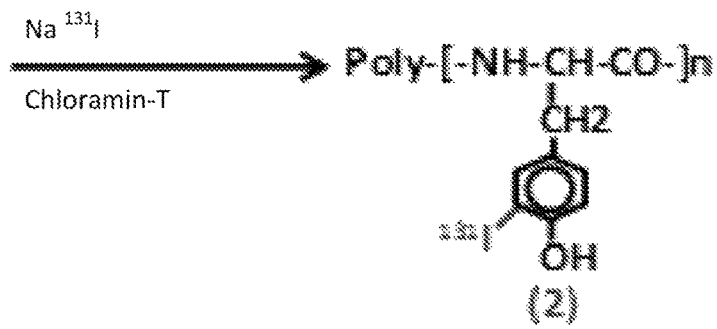
Figure 6:
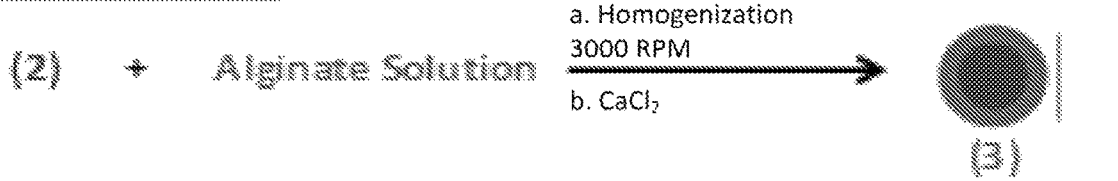
Figure 6:
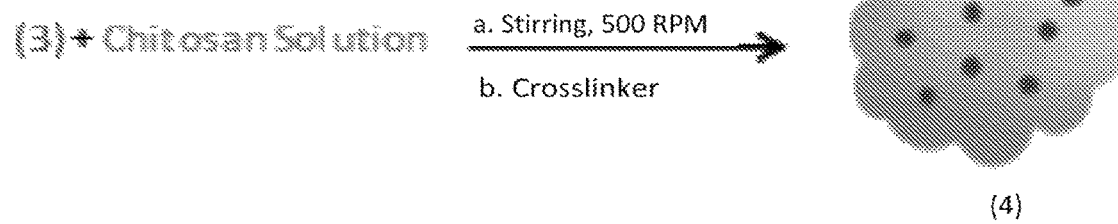

From the preliminary data as seen in Example 2 and FIG. 5, the two concepts of conjugation to high-molecular weight molecules and encapsulation may reduce the leakage of small molecules from the chitosan hydrogels. These two concepts may be applied to prevent leakage of $^{131}$I from the implants. Poly-tyrosine may be used as a high molecular weight molecule to increase the efficiency of iodination (using Na$^{131}$I and chloramines-T); and the $^{131}$I-Polytyrosine may be encapsulated in calcium-alginate microparticles. Na$^{131}$I, $^{131}$I-poly-tyrosine and encapsulated $^{131}$I-poly-tyrosine may be dispersed in chitosan hydrogels (see FIG. 6); and the release of radioactivity to the media from each preparation may be tested in vitro. Hydrogels loaded with different radioactive entities may be incubated in PBS for 4 weeks and the medium may be sampled and tested for radioactivity at 1, 2, 6, 12 and 24 hours, as well as at 3, 7, 14, 21 and 28 days.

The degradation rate and leakage of radioactivity to the tissue may be characterized in vivo. Implants as described in FIG. 6 may be produced but may use $^{131}$Iodine (radioactive) or $^{127}$Iodine (cold) for the iodination. The cold implants may be used to study the degradation of the implant and the radioactive implants may be used to assess leakage from the implants. The cold implant may be implanted subcutaneously into 15 mice, and 3 mice may be sacrificed at different time points (1, 7, 14, 28 and 56 days). The implant may be retrieved and the weight loss of the implant compared to a comparison implant that was not implanted may be calculated. The weight loss may be assessed based on the dry weight implant, as the degree of swelling (water content) is expected to change over time.

In addition, the leakage of radioactivity to adjacent tissue from radioactive implants may be studied after subcutaneous implantation in 5 mice. The mice may be imaged at different time points (0, 1, 7, 14, 28 and 56 days). The biodistribution of radioactivity may be determined after the implantation as previously described.

Prophetic Example 2

The efficacy of prototype radioactive hydrogels ($^{131}$I-conjugated to poly-tyrosine, encapsulated in microparticles and dispersed in injectable hydrogel) in inhibition of tumor growth in vitro and in vivo and the prevention of glioma recurrence in vivo compared to conventional radiotherapy may be assessed.

The dose of $^{131}$I loaded to the hydrogels may be optimized and the radioactive dose at different distances from the radioactive source may be calculated. The dose may be optimized to match the clinically used dose using tumor absorbed dose calculations based on the assumption of dynamic tumor mass using the Gompertz equation. This may help adjust the tissue penetration of the treatment to within about 1 cm beyond the surgical margin.

The effect of the radioactive hydrogels on glioma cell-lines growth in vitro compared to conventional radiotherapy may be assessed. Glioma cell lines (GL261, U87 and D54) may be seeded in plates, cold-hydrogels and radioactive-hydrogels may be implanted in the middle of the plate for 0, 1, 4, 8, 24 and 48 hours, and the cells may be analyzed for different endpoints including: survival (MTT assay), apoptosis (annexin-PI assay), cell cycle (PI binding to DNA assay), and the effect on different cell signaling pathways including proliferative pathways (PI3K and MAPK), apoptosis (caspases and PARP), cell cycle (cyclins, CDKs and pRb) by immuno-blotting.

The effect of the radioactive hydrogels on glioma progression and recurrence in vivo may be assessed. Orthotopic glioma tumors may be induced by injecting U87 cells, which were genetically engineered to express luceferase and GFP (U87-GFP-Luc), into the brains of six-week-old nude mice. Tumor progression may be assessed by bioluminescence imaging. The efficacy of the radioactive hydrogel may be compared to single-high-dose and fractionated-low-dose external beam radiotherapy. Moreover, the efficacy of a single-high-dose external beam may be tested in combination with radioactive-hydrogels compared to each alone.

To assess tumor growth, 100,000 U87-GFP-Luc cells may be injected to each of 60 mice, and after three weeks when tumor progression may be confirmed by bioluminescence imaging, mice may be randomized into six cohorts of 10 animals each, which may be treated with: a) non-treated control; b) implantation of cold-hydrogel; c) treatment with single high-dose external beam radiation (8Gy at weeks 0=total of 8Gy); d) treatment fractionated low dose external beam radiation (2Gy×at weeks 0,1, 2 and 3=Total 8Gy); e) treatment with injection of radioactive hydrogels with a total-dose of 8Gy into the tumor; and f) treatment with 4Gy external beam radiation followed by implantation of radioactive hydrogels loaded with 4Gy into the tumor (total dose 8Gy). Tumor growth, bodyweight and survival of the mice may be monitored twice a week for 4 weeks.

To assess tumor recurrence, 10,000 U87-GFP-Luc cells (10% of the amount in the tumor growth models) may be injected to the brains of the mice to mimic micro-residual disease. The cells may grow for one week to allow colonization, and then mice may be randomized into six cohorts and treated as above in the tumor growth model. Tumor growth, body weight and survival of the mice may be monitored once a week for 8 weeks.

Potential side effects of the radioactive hydrogels in adjacent normal tissues and distant organs may be characterized compared to traditional radiotherapy. Non tumor bearing mice (90 mice) may be randomized into 6 cohorts of 15 mice each, and treated as described above. Three mice may be sacrificed from each cohort at days 1, 8, 16, 23 and 29; moreover 3 mice may be sacrificed at day 0 as a control. Mice may be fixed and tissue specimens from the brain, bone marrow, intestine, skin, and other organs may be examined for tissue damage and foreign body reaction using histopathology.

The examples described herein are included to demonstrate preferred embodiments of the invention. It should be appreciated by those of skill in the art that the techniques disclosed in the examples included herein represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

What is claimed is:

1. A method of delivering radiotherapy comprising:
    resecting a soft tissue sarcoma to create a surgical cavity; and
    injecting a radioactive hydrogel into the surgical cavity, the radioactive hydrogel comprising:
        at least one beta emitting radioisotope;
        at least one high molecular weight molecule conjugated to the radioisotope, wherein the high molecular weight molecule has a molecular weight greater than about 4 kD;
        at least one microparticle encapsulating the radioisotope conjugated to the high molecular weight molecule, wherein the microparticle is between about 1 µm to about 8 µm in size; and
        an injectable hydrogel,
        wherein the at least one microparticle is disbursed and immobilized within the injectable hydrogel, and
        wherein the at least one beta emitting radioisotope is retained within the hydrogel until the radiation has decayed, wherein radiation is released from the hydrogel for a period of about 5 days to about 20 days after injection, and wherein the radioactive hydrogel begins to biodegrade after the radioisotope has decayed and is not removed from the surgical cavity.

2. The method of claim 1, wherein the at least one beta emitting radioisotope is selected from $^{131}$I, and $^{126}$I.

3. The method of claim 1, wherein the at least one high molecular weight molecule is selected from poly-tyrosine, serum albumin, and polymers with chelating residues.

4. The method of claim 1, wherein the at least one microparticle is selected from alginate, poly-acrylate, poly-metacrylate, poly-carbophil, Carbopol, poly-styrene, and poly-sulfonate.

5. The method of claim 1, wherein the injectable hydrogel comprises chitosan.

6. The method of claim 1, wherein the soft tissue sarcoma is selected from the group consisting of glioma and breast cancer.

* * * * *